US006926744B1

(12) United States Patent
Bos et al.

(10) Patent No.: US 6,926,744 B1
(45) Date of Patent: Aug. 9, 2005

(54) INTRAOCULAR IMPLANT

(75) Inventors: Gilles Bos, La Balme De Sillingy (FR); Denis Gantin, Bonneville (FR)

(73) Assignee: Corneal Industrie, Pringy (FR)

( * ) Notice: Subject to any disclaimer, the term of this patent is extended or adjusted under 35 U.S.C. 154(b) by 251 days.

(21) Appl. No.: 10/009,936

(22) PCT Filed: Jul. 6, 2000

(86) PCT No.: PCT/FR00/01940

§ 371 (c)(1),
(2), (4) Date: Dec. 10, 2001

(87) PCT Pub. No.: WO01/03610

PCT Pub. Date: Jan. 18, 2001

(30) Foreign Application Priority Data

Jul. 8, 1999 (FR) .................................. 99 08837

(51) Int. Cl.[7] .............................................. A61F 2/16
(52) U.S. Cl. ..................... 623/611; 623/6.16; 623/6.38; 623/6.46
(58) Field of Search .............................. 623/6.16, 6.17, 623/6.39, 6.46, 6.11, 6.49, 4.1, 6.38, 6.43

(56) References Cited

U.S. PATENT DOCUMENTS

| 4,664,666 A |   | 5/1987 | Barrett |            |
|-------------|---|--------|---------|------------|
| 4,738,680 A | * | 4/1988 | Herman  | ... 623/6.11 |
| 4,936,850 A |   | 6/1990 | Barrett |            |
| 5,141,507 A | * | 8/1992 | Parekh  | ... 623/6.46 |

(Continued)

FOREIGN PATENT DOCUMENTS

DE  1 108 402 A2 * 6/2001 ............. A61F 2/16

(Continued)

OTHER PUBLICATIONS

*Preventing posterior capsule opacification by creating a discontinuous sharp bend in the capsuyle*, Okihiro Nishim, MD, et al., Nishi Eye Hospital, Osaka, Japan, Dec. 1, 1998, XP 000900073, pp. 521-526.

(Continued)

*Primary Examiner*—David H. Willse
*Assistant Examiner*—Javier G. Blanco
(74) *Attorney, Agent, or Firm*—Cohen, Pontani, Lieberman & Pavane

(57) ABSTRACT

The invention relates to an intraocular implant comprising an optical portion presenting an anterior optical surface (24) and a posterior optical surface (26), and at least one haptic element (12, 14), each haptic element presenting a connection zone at the periphery of the optical portion. Outside the connection zones, the optical portion further comprises a cylindrical side face of diameter D1 connected to the posterior optical surface of the optical portion. The posterior optical surface (26) is bounded by a circle of diameter D1. In each connection zone, the implant comprises a radial extension (30) presenting an anterior face (30a), a posterior face (30b), and a side face (30c) substantially disposed on a ruled surface of diameter D2 where D2>D1, and presenting a length h' in the direction of the axis, said length h' being substantially equal to h. The posterior face (30b) of each extension is disposed on the spherical cap containing the posterior optical surface. Each haptic element (12, 14) is connected to the optical portion (10) via the anterior face (30a) of the corresponding extension, on the outside of the anterior optical surface (24).

8 Claims, 3 Drawing Sheets

U.S. PATENT DOCUMENTS

| | | | |
|---|---|---|---|
| 5,275,624 A | | 1/1994 | Hara et al. |
| 5,476,513 A | * | 12/1995 | Brady et al. .................. 623/6.4 |
| 5,713,958 A | * | 2/1998 | Weiser ....................... 623/6.51 |
| 5,928,282 A | | 7/1999 | Nigam |
| 6,468,306 B1 | * | 10/2002 | Paul et al. .................. 623/6.16 |
| 6,558,419 B1 | * | 5/2003 | Pham et al. ................ 623/6.16 |
| 2003/0120342 A1 | * | 6/2003 | Green ........................ 623/6.16 |
| 2003/0158599 A1 | * | 8/2003 | Brady et al. ............... 623/6.37 |
| 2003/0204257 A1 | * | 10/2003 | Southard ................... 623/6.46 |

FOREIGN PATENT DOCUMENTS

| | | | | |
|---|---|---|---|---|
| EP | 0 391 452 | | 8/1984 | ............. A61F 2/16 |
| EP | 0 215 468 | | 9/1986 | ........... A61F 2/174 |
| EP | 0 507 292 A1 | | 4/1992 | ............. A61F 2/16 |
| FR | 2 668 922 | | 11/1990 | ............. A61F 2/16 |
| FR | 2773705 A1 | * | 7/1999 | ............. A61F 2/16 |
| FR | 2 819 713 A1 | * | 7/2002 | ............. A61F 2/16 |
| FR | 2821268 A1 | * | 8/2002 | ............. A61F 2/16 |
| WO | WO 97/41805 | | 11/1997 | ............. A61F 2/16 |
| WO | WO 98/56315 | | 12/1998 | ............. A61F 2/16 |
| WO | WO 200189425 A1 | * | 11/2001 | ............. A61F 2/16 |

OTHER PUBLICATIONS

International Search Report dated Sep. 8, 2000 (in French and English).

Preliminary Examination Report dated Apr. 20, 2001 (in French).

* cited by examiner

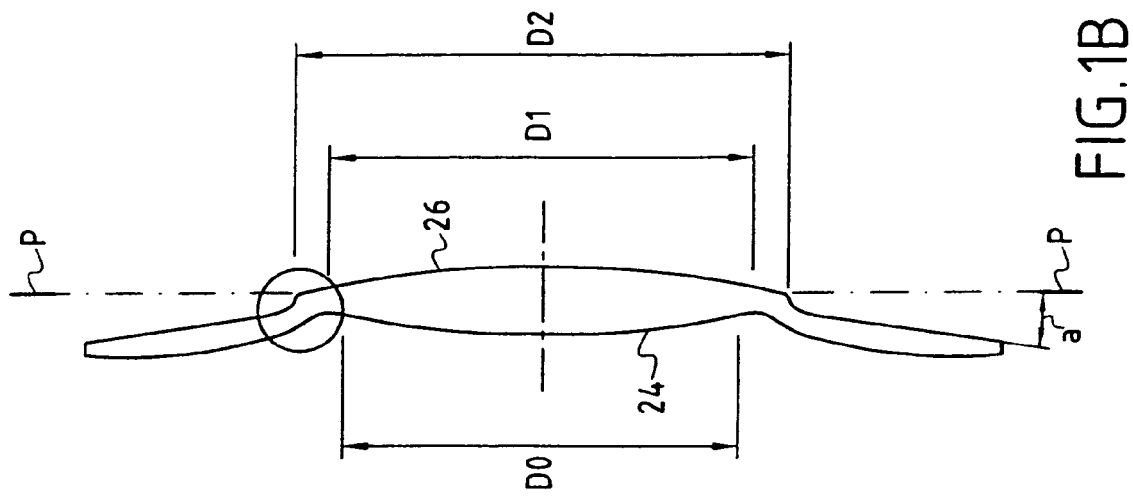
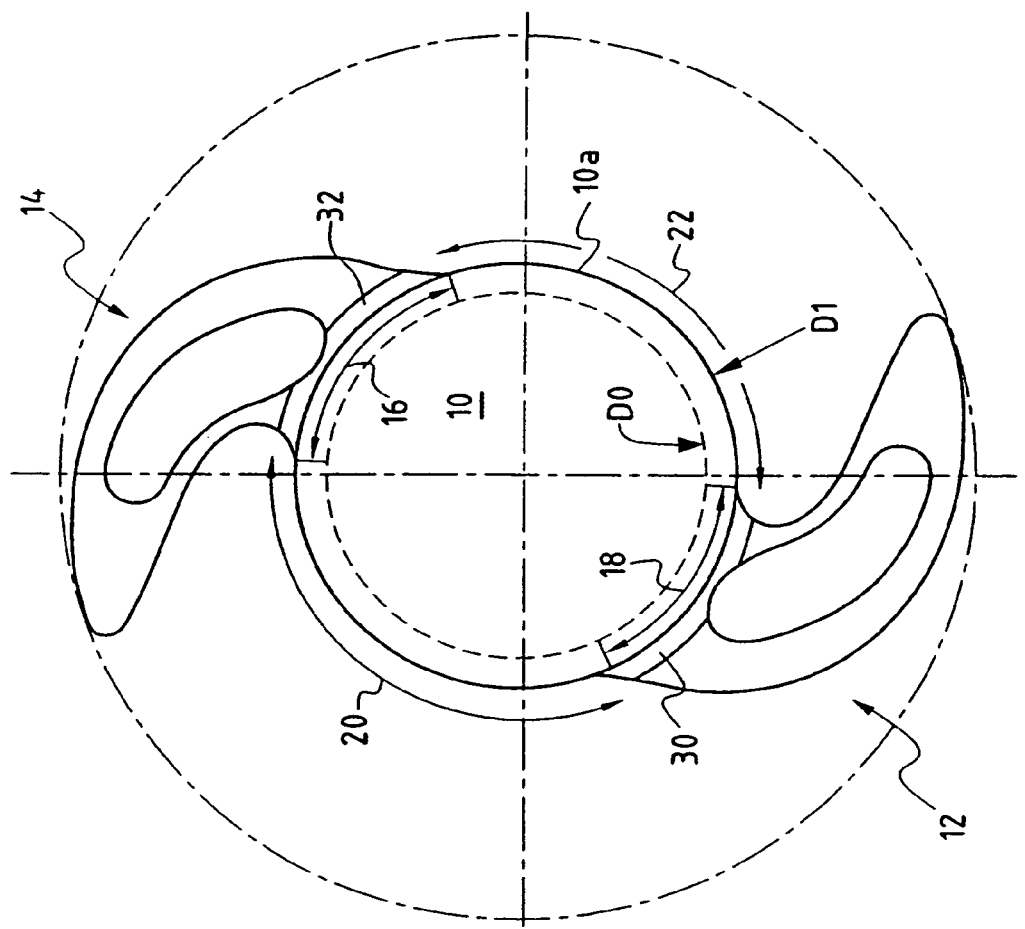
FIG.1B
FIG.1A

INTRAOCULAR IMPLANT

PRIORITY CLAIM

This is a U.S. national stage of application No. PCT/FR00/01940, filed on Jul. 6, 2000. Priority is claimed on that application and on the following application(s) Country: France, Application No.: 99 08837, Filed: Jul. 8, 1999.

The present invention relates to an intraocular implant of the "square-edged" type.

Intraocular implants are well known. They are essentially constituted by a substantially circular optical portion and by a haptic portion which serves to hold the optical portion inside the eye in such a manner that the optical axis of the optical portion of the implant coincides with the optical axis of the eye. The free ends of the haptic portion bear against the inside wall of the eye in order to develop a resilient return force ensuring that the implant is held in place.

One of the main uses of such intraocular implants consists in putting the implant in the capsular bag after ablation of the lens during a cataract operation.

It is known that cellular proliferation after cataract surgery is the main post-operative complication of that type of surgery. Such cellular proliferation can cause the posterior portion of the capsular bag to become completely opaque. It is then necessary to perform capsulotomy using an ND-Yag laser.

According to data provided by the literature in this matter, the capsulotomy rate can be as high as 50% within 3 years from the operation, in particular with implants made of rigid material of the PMMA type.

Studies conducted in particular by Nishi et al. which are the subject of a publication in the "Journal of Cataract Refract Surgery", volume 25, April 1999, seem to indicate that it is possible to prevent the cells proliferating on the posterior capsule by means of the edge of the optical portion of the implant acting on the posterior capsule, when the optical portion includes a "square" edge. The term "square edge" has been adopted to define the optical-portion edges having an edge surface which forms an angle of close to 90 degrees (°) relative to the optical surface and which retains a sharp appearance.

In addition, it is known that in intraocular implants, which are now often made in a single piece, the haptic portion is connected to the periphery of the optical portion via a "connection zone". The term "single-piece implant" refers to an implant made as a single piece, even if the optical and the haptic portions are made of different materials. For the implants on which the above-mentioned studies were based, the haptic portion is constituted by two loops of narrow width such that the connection zones constitute a very small percentage only of the entire periphery of the optical portion. Under such circumstances, it will be understood that the square edge of the optical portion is effective in preventing cells from proliferating on the posterior capsule because the square optical edge is interrupted only in zones of very limited length corresponding to the connection zones. However, such zones do allow cells to proliferate.

It will be understood that the problem is even greater where the connection zone(s) represent a significant percentage of the total length of the periphery of the optical portion. In the connection zone(s), proliferation cannot be prevented since the optical portion does not have square edges. Implants having connection zone(s) that represent a significant fraction of the periphery of the optical portion are becoming more and more common, in particular when single-piece implants are made of a flexible material of the "hydrogel" type or of the "silicone" type. That type of connection zone can also be found in implants made of a rigid material, e.g. of the PMMA type, when the haptic contact portion for contact with the inside wall of the eye is constituted substantially by a ring shape connected to the optical portion by a single substantially radial arm having a width that is necessarily relatively great to ensure a suitable connection between the optical portion and the contact ring of the haptic portion.

It should also be recalled that the surgical practice of putting the implant in place inside the eye is tending to make use of an incision in the cornea that is of smaller and smaller size. When designing intraocular implants, it is therefore necessary to ensure that the overall thickness of the implant remains small so as to enable the implant to be implanted through an incision of small size, with this constraint applying both to the optical portion and to the haptic portion and even to the connection between these two portions. This is particularly, but not exclusively, true of implants having an optical portion that is made of a flexible material enabling the optical portion to be folded on a diameter.

An object of the present invention is to provide an intraocular implant for a capsular bag, the implant being of the square-edged type, thus enabling the proliferation of cells on the posterior capsule to be effectively prevented, in particular in the case where the connection zone(s) for connecting the haptic portion to the optical portion are of significant length, while the thickness of the implant is kept as thin as possible.

To achieve this object, the invention provides an intraocular implant for a capsular bag, which implant comprises an optical portion presenting an anterior optical surface and a posterior optical surface, and at least one haptic element, each haptic element presenting a connection zone at the periphery of the optical portion, said implant being characterized in that:

outside the connection zones, the optical portion further comprises a cylindrical side face of diameter D1 connected to the posterior optical surface of the optical portion and parallel to the optical axis of the implant, the length of the side face along the axis being equal to h;

the posterior optical surface is bounded by a circle of diameter D1;

and in that it further comprises, in each connection zone, a radial extension presenting an anterior face, a posterior face, and a side face substantially disposed on a ruled surface of diameter D2 where D2>D1, and presenting a length h' in the direction of the axis, said length h' being substantially equal to h;

the posterior face of each extension is disposed on the spherical cap containing the posterior optical surface;

each haptic element being connected to the optical portion via the anterior face of the corresponding extension, on the outside of the anterior optical surface, whereby each extension constitutes a step formed by the offset between the posterior optical surface of the optical portion and the connection zone of the haptic element, the side face of each extension forming a square-edged portion with the posterior optical surface.

It will be understood that because of the presence of radial extension(s) at the connection zone(s), which by means of their side walls constitute respective steps resulting from the offset between the posterior optical surface of the optical portion and the connection zone of the haptic element, continuity of the square edge is obtained over the entire periphery of the optical portion. In addition, the fact that the "root(s)" of the haptic portion(s) is/are connected to the anterior face of the extension(s) prevents any increase in the overall thickness of the implant.

In a preferred implementation, the spherical cap, on which are disposed the posterior optical surface of the optical portion and the posterior faces of the step-forming extensions, has a radius lying in the range 11 millimeters (mm) to 13 mm.

The studies performed for developing the present invention have shown that it is this diameter that provides the best contact between the posterior capsule and the posterior optical surface of the implant, thus preventing cells from proliferating. This ensures that the posterior capsule, which is very fine, being about microns ($\mu$m) thick, is tensioned in the zone defined by contact with the square edge of the implant. The risks of folds forming in the posterior capsule and thus the risks of cells proliferating along said folds are thus avoided.

Also preferably, the haptic portion(s) form(s) an angle a lying in the range 5° to 12° relative to the optical plane and directed towards the anterior face of the implant.

This tilt tends to press the posterior optical surface of the implant and the posterior face of the step-forming extensions against the posterior capsule.

Other characteristics and advantages of the invention will appear better on reading the following description of embodiments of the invention given as non-limiting examples. The description refers to the accompanying figures, in which:

FIG. 1A is a front view of a first intraocular implant of the invention;

FIG. 1B is a side view of the implant of FIG. 1A;

Figure 1C:
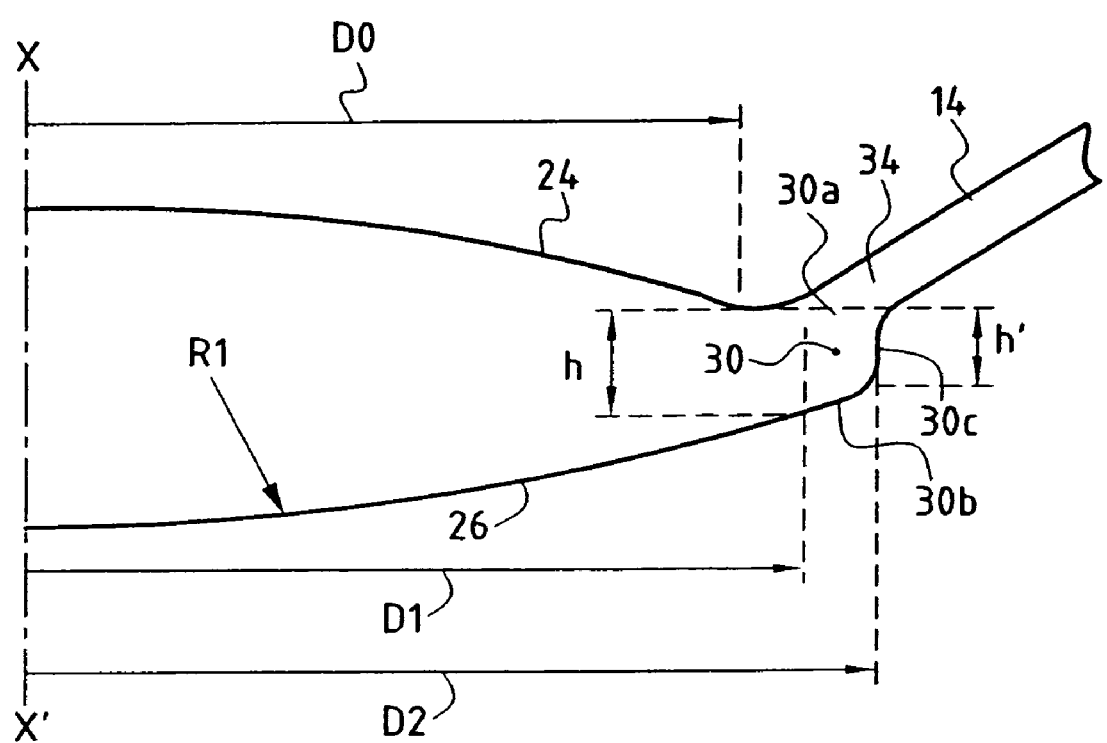
FIG. 1C is a fragmentary view of FIG. 1B showing in more detail the connection between the haptic portion and the optical portion of the implant.

With reference firstly to FIG. 1A, which shows an intraocular implant designed to be placed in the capsular bag, it can be seen that said intraocular implant comprises an optical portion 10 presenting a circular periphery 10a, and two haptic elements respectively referenced 12 and 14. The haptic elements 12 and 14 are connected to the periphery 10a of the optical portion via connection zones which are indicated by double-headed arrows 16 and 18. It can also be seen that the periphery 10a is free over the remainder of its length, as indicated by double-headed arrows 20 and 22. In these zones, the side wall 10a of the optical portion 10 is substantially cylindrical and is connected to the posterior optical surface in order to form the "square edge", said side wall extending towards the inner optical surface.

As already explained, it is easy to provide a square edge for the free zones of the periphery 20 and 22. The embodiment of the invention which enables a square edge to also be obtained in the connection zones 16 and 18, while preventing any increase in the overall thickness of the implant, is described below in more detail, with reference more particularly to FIGS. 1B and 1C.

FIG. 1B shows the anterior optical surface 24 and the posterior optical surface 26 which define the optical portion 10. The anterior optical surface 24 is constituted by a concave or convex spherical cap and is bounded by a circle of diameter D0 centered on the optical axis XX' of the implant. The posterior optical surface 26 is bounded by a circle of diameter D1 which is preferably greater than D0.

The circle of diameter D1 constitutes the physical boundary of the optical portion or optical edge outside the connection zones. The posterior optical surface 26 is convex or plane.

To enable the square edge to be formed in the connection zones 16 and 18, radial extensions 30 and 32 are provided in said connection zones, facing the connection zones, as shown more clearly in FIG. 1C. Each extension 30 or 32 comprises an anterior face 30a, a posterior face 30b, and a side face 30c which together constitute a step as described below, thereby, with the posterior face 30b, constituting the square edge in the connection zone. Furthermore, the posterior face 30b of the extension 30 is disposed on the same spherical cap as the posterior optical surface 26, the spherical cap having a radius R1. The side face 30c of the extension 30 which forms part of the step and the square edge is substantially disposed on a ruled surface of axis XX' and of diameter D2 that is greater than the diameter D1 defining the posterior optical surface 26. The ruled surface can be compared to a cylinder, a cone, a truncated cone, etc. On the portions of its periphery 10a corresponding to the free zones 20 and 22, the optical edge presents a length h in the direction of the axis XX'. In the extension zones 30 and 32, the step constituted by the side wall 30c presents a length h' in the direction of the axis XX', which length is of course slightly shorter than h.

FIG. 1C also shows connection of the haptic element 14 to the periphery of the optical portion. Connection of the haptic element 12 is identical. The root 34 of the haptic element 14 is connected to the anterior face 30a of the extension 30, on the outside of the anterior optical surface 24, i.e. on the outside of the circle of diameter D0. Thus, the optical properties of the optical portion are not altered since the roots 34 of the haptic portions are on the outside of the anterior optical surface. Conversely, since the roots are connected to the anterior faces of the extensions 30 and 32, they do not increase the overall thickness of the implant, while making possible the presence of steps 30 and 32 which define the square edges in the connection zones by means of their side faces 30c and their posterior faces 30b.

In a preferred embodiment, the diameter D0 is about 5 mm, the diameter D1 is about 6 mm, and the diameter D2 is about 6.5 mm. The length h' corresponding to the steps in the connection zones is not less than 120 $\mu$m and preferably lies in the range 120 $\mu$m to 200 $\mu$m. As a result, the optical edge of length h is slightly greater than that value.

The studies performed show that said length h' of the step is sufficient to obtain the desired result, i.e. to prevent cells proliferating on the posterior capsule. Said length h, h' is linked to the size of cells that are capable of proliferating on the posterior capsule.

This result is further improved due to the fact that the radius R1 preferably lies in the range 11 mm to 13 mm, thereby ensuring the best possible contact with the posterior capsule, thus tensioning said capsule and preventing any risk of folds forming. With the radius of the posterior optical surface defined in this way, the power of the implant is determined by appropriately selecting the radius of the anterior optical surface. This is possible for standard optical powers for an implant.

Figure 2B:
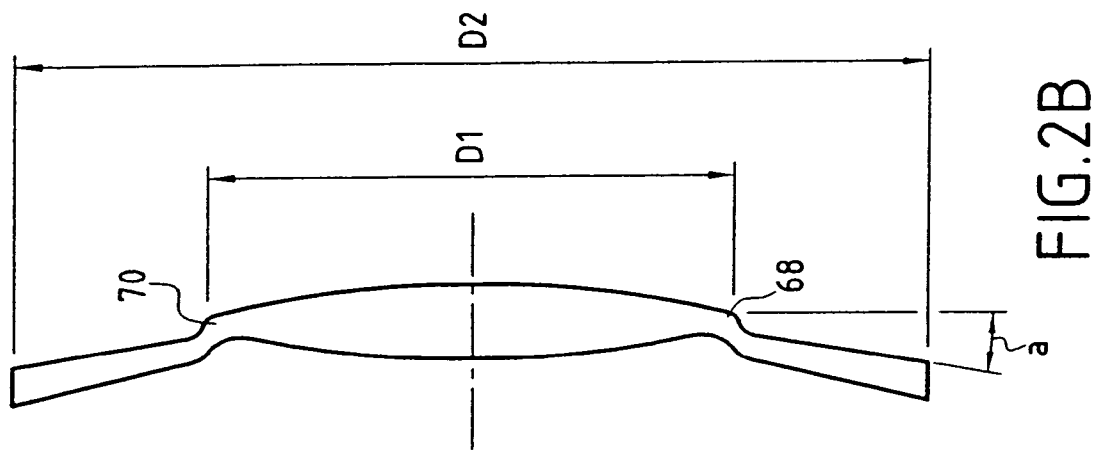
FIG. 2B is a side view of the implant of FIG. 2A.

As shown more clearly in FIG. 1B, the haptic arms 12 and 14 present, preferably relative to the optical plane PP', an angle of tilt a that lies in the range 5° to 12°. The angle a is preferably close to 10°. In FIG. 2B, its value is 9.5°. This tilting of the haptic arms towards the front, tends to press the posterior optical surface, with its extensions, more effectively against the posterior capsule.

In this embodiment, the implant is in a single piece and is made of a flexible material. Each haptic element is constituted by two arms connected together at their contact end. The two arms include a common connection zone.

Figure 2A:
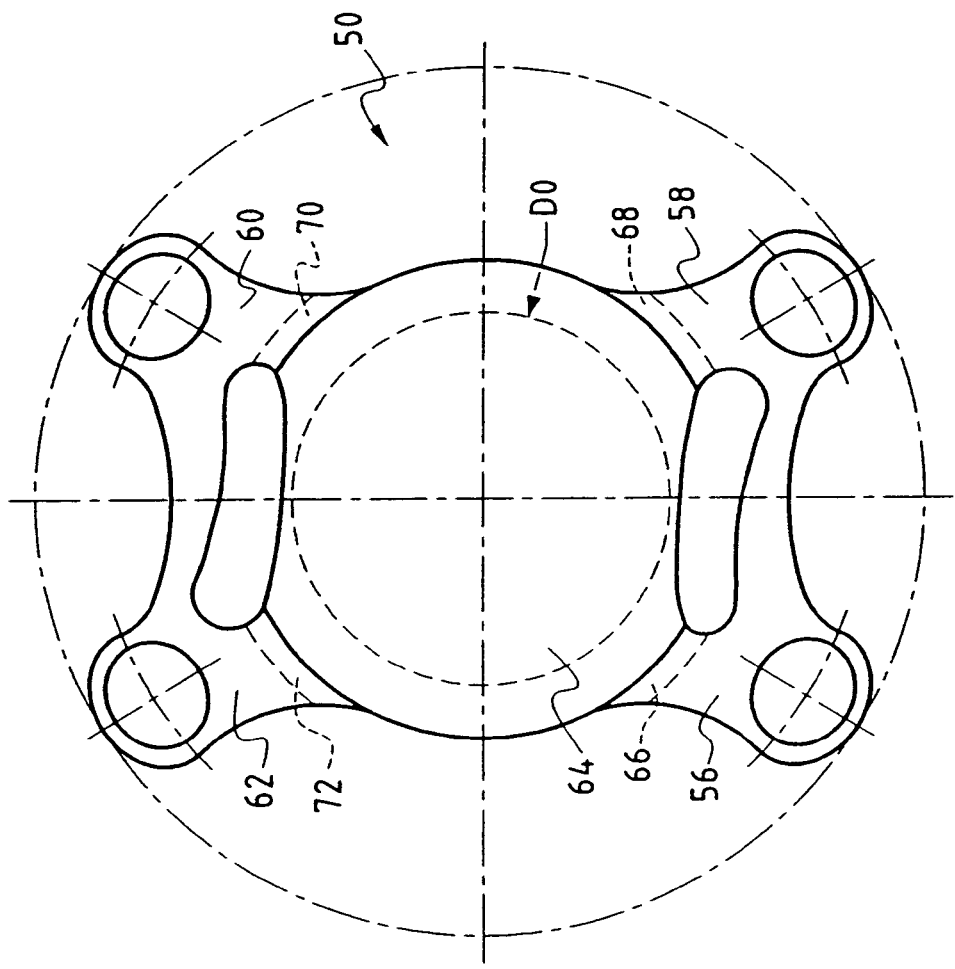
FIG. 2A is a front view of a second embodiment of an implant having square edges when viewed from the front.

The implant 50 shown in FIGS. 2A and 2B differs from the implant in FIGS. 1A and 1C only in the shape of its haptic portion. The haptic portion is constituted by two haptic assemblies 52 and 54 each formed by two haptic members 56 & 58 and 60 & 62 connected to the periphery of the optical portion 64. In this case, there are thus four connection zones corresponding to four haptic members. A radial extension is situated in each connection zone, the radial extensions being referenced 66, 68, 70, and 72. The radial extensions 66, 68, 70, and 72 have exactly the same shape as the two radial extensions 30 and 32 in FIGS. 1A and 1C.

The implant can be made either of a rigid material such as PMMA, or of a flexible material such as silicone or acrylics. For a flexible material, hydrophobic or hydrophilic pHEMA can be used.

What is claimed is:

1. A single-piece intraocular implant for a capsular bag, said implant comprising:
   a circular optical portion having
      an optical axis,
      a periphery having at least one connection zone extending over a significant part thereof,
      an anterior optical surface,
      a cylindrical peripheral surface having a diameter, and being disposed parallel to said optical axis, said cylindrical peripheral surface having a length h measured parallel to said optical axis, said cylindrical peripheral surface being free of any other portion of the implant except in said connection zone, and
      a posterior optical surface defined by a spherical cap;
   at least one haptic element, each said haptic element having a posterior face and a connection end for connection to a respective one of said connection zones of said periphery of said optical portion; and
   at least one radial extension disposed completely within each said connection zone between the circular optical portion and the haptic element and projecting out of said cylindrical peripheral surface, each said radial extension having
      an anterior face,
      a side face disposed on a ruled surface having a diameter D2, said diameter D2 being greater than said diameter of said cylindrical peripheral surface, said side face having a length h' measured parallel to said optical axis and being substantially equal to said length h of the cylindrical peripheral surface, and
      a posterior face disposed in said spherical cap;
   wherein said connection end of each said haptic element is connected to said periphery of said optical portion via said anterior face of a corresponding one of said radial extensions outside said anterior optical surface of said circular optical portion; and
   whereby each said radial extension constitutes a step formed by the offset between said posterior optical surface of said circular optical portion and said posterior face of each said haptic element, and said side face of each said radial extension forms a square-edged portion with said posterior face of said radial extension.

2. An implant according to claim 1 characterized in that the length h of the cylindrical peripheral surface and the length h' of the side faces (30c) in the direction of the optical axis are not less than 150 μm.

3. An implant according to claim 2, characterized in that the anterior optical surface is bounded by a circle having a diameter D0 that is less than said diameter of said cylindrical peripheral surfaces.

4. An implant according to claim 1, wherein the spherical cap, on which are disposed the posterior optical surface of the circular optical portion and the posterior faces of the radial extensions, has a radius lying in the range of 11 mm to 13 mm.

5. An implant according to claim 4, characterized in that the anterior optical surface is bounded by a circle having a diameter D0 that is less than said diameter of said cylindrical peripheral surface.

6. An implant according to claim 1, wherein each haptic element forms an angle a lying in the range of 5° to 12° relative to the optical plane and directed towards said anterior face.

7. An implant according to claim 6, characterized in that the anterior optical surface is bounded by a circle having a diameter D0 that is less than said diameter of said cylindrical peripheral surface.

8. An implant according to claim 1, characterized in that the anterior optical surface is bounded by a circle having a diameter D0 that is less than the diameter.

* * * * *